United States Patent [19]

Bhagat et al.

[11] 4,383,533
[45] May 17, 1983

[54] APPARATUS FOR DETERMINING CHANGES IN LIMB VOLUME

[75] Inventors: Alan M. Lovelace, Administrator of the National Aeronautics and Space Administration, with respect to an invention of Pramode K. Bhagat; Vic C. Wu, both of Lexington, Ky.

[73] Assignee: The United States of America as represented by the Administrator of the National Aeronautics and Space Administration, Washington, D.C.

[21] Appl. No.: 233,270

[22] Filed: Feb. 10, 1981

[51] Int. Cl.³ .............................................. A61B 5/00
[52] U.S. Cl. .................................. 128/660; 128/663; 73/597
[58] Field of Search .................... 73/597; 128/660, 663

[56] References Cited

U.S. PATENT DOCUMENTS

| | | | |
|---|---|---|---|
| 3,888,238 | 6/1975 | Meindl et al. | 128/660 |
| 4,024,760 | 5/1977 | Estrada, Jr. | 73/861.31 |
| 4,074,564 | 2/1978 | Anderson | 73/602 |
| 4,102,186 | 7/1978 | Brown | 73/861.31 |
| 4,105,018 | 3/1978 | Greenleaf et al. | 73/602 |
| 4,338,948 | 7/1982 | Perez-Mendez et al. | 128/660 |

OTHER PUBLICATIONS

P. K. Bhagat et al., "Microprocessor-Controlled Ultrasonic Plethysmograph".

*Primary Examiner*—Richard J. Apley
*Assistant Examiner*—George Yanulis
*Attorney, Agent, or Firm*—Carl O. McClenny; John R. Manning; Marvin F. Matthews

[57] ABSTRACT

Measuring apparatus for determining changes in the volume of limbs or other body extremities by determining the cross-sectional area of such limbs may comprise a transmitter (10) including first and second transducers (11, 12) for positioning on the surface of the limb at a predetermined distance therebetween, and a receiver (20) including a receiver crystal (21) for positioning on the surface of the limb. The distance between the receiver crystal and the first and second transducers are represented by respective first and second chords ($d_1$, $d_2$) of the cross-section of the limb (C) and the predetermined distance between the first and second transducers is represented by a third chord ($d_3$) of the limb cross-section (C).

The measuring apparatus may also include a Pinger (10) and associated electrical circuitry for generating acoustic pulses at the first and second transducers (11, 12) for propagation along the first and second chords ($d_1$, $d_2$) to derive at the receiver (20) first and second signals related to the travel time of the acoustic pulses along these chords. A computer (30) is connected to the receiver (20) for computing the area of the limb cross-section (C) utilizing these first and second signals.

10 Claims, 3 Drawing Figures

APPARATUS FOR DETERMINING CHANGES IN LIMB VOLUME

ORIGIN OF THE INVENTION

The invention described herein was made in the performance of work under a NASA Contract and is subject to the provisions of Section 305 of the National Aeronautics and Space Act of 1958, Public Law 85-568 (72 Stat. 435; U.S.C. 2457).

TECHNICAL FIELD

The present invention pertains to apparatus for measuring changes in the volume of portions of the human body, and particularly to plethysmography. Specifically, it pertains to apparatus utilizing ultrasonics for nonintrusive determination of limb volume changes. It pertains to apparatus suitable for nonintrusive determination of changes in limb volume of individuals placed in unusual environments, i.e. space or underwater.

BACKGROUND ART

There are a number of plethysmographs which have been used to measure changes in volume or volumetric flow of portions of the body. In U.S. Pat. No. 3,570,474, apparatus for determining body volume changes is disclosed which utilizes a rigid tubular member for surrounding a portion of a body extremity leaving an annular chamber therearound. The chamber is in communication with a flowmeter which is sensitive to fluid flow into or out of the tube chamber, caused by volume changes in the body extremity enclosed within the tube. Another plethysmograph shown in U.S. Pat. No. 3,381,682 is of the capacitance type. However, the capacitance plethysmograph suffers from sensitivity to environmental conditions and capacitance changes due to variations in skin moisture and dielectric composition of the flesh. The capacitance plethysmograph requires custom-made capacitance transducers which are not easy to calibrate.

A few ultrasonic plethysmographs have also been developed for determining various body changes. One such system is shown in U.S. Pat. No. 3,888,238 for detecting blood flow at various depths under a transducer element. This system detects the flow of blood particles through blood vessels and provides a video output which indicates the flow of blood particles through the vessels. The video output signal is sampled in a display form which indicates the depth, location and the size of underlying blood vessels.

In U.S. Pat. No. 4,095,597, a system is shown for measuring cross-sectional fluctuations of blood vessels through an ultrasound-Doppler method. In this arrangement, a single ultrasound transmitter/receiver is used for projecting ultrasound into the fluid and for receiving the ultrasound reflected by the fluid. Dopler apparatus is provided for producing Dopler signals and for detecting intensity and amplitude fluctuations thereof.

Other ultrasonic apparatus for measuring volumetric flowrates of fluids through pipelines or other conduits are illustrated in U.S. Pat. Nos. 4,024,760, and 4,102,186. However, these devices are not concerned with changes in the volume of the conduit since the cross-sectional area of the conduits is assumed to be constant.

DISCLOSURE OF THE INVENTION

In the present invention, a plethysmograph is disclosed for measuring changes in volume of limbs or other extremities of the human body. The plethysmograph of the present invention utilizes ultrasonic devices in combination with a microprocessor and related digital circuitry. Two ultrasonic transmitter/transducers and one receiver are placed externally upon the limb and two very accurate chord length measurements are obtained from a knowledge of the speed of sound in flesh. The system operates by assuming a circular cross-section of the limb, the area of which can be determined by the derivation of equations for solving circular area when two chord lengths are known. The equations are simulated on the microprocessor and the cross-sectional area (an indication of limb volume) is automatically calculated and displayed.

The system of the present invention provides measurement of limb volume in a noninvasive manner and is virtually free of inaccuracies arising from body temperature changes and timing errors. The system does not confine limb movement, requires no calibration, and is simple to operate, the calculations being automatically performed by the microprocessor. Other objects and advantages of the invention will be apparent from reading the description which follows in conjunction with the accompanying drawings.

DESCRIPTION OF A PREFERRED EMBODIMENT

Figure 1:
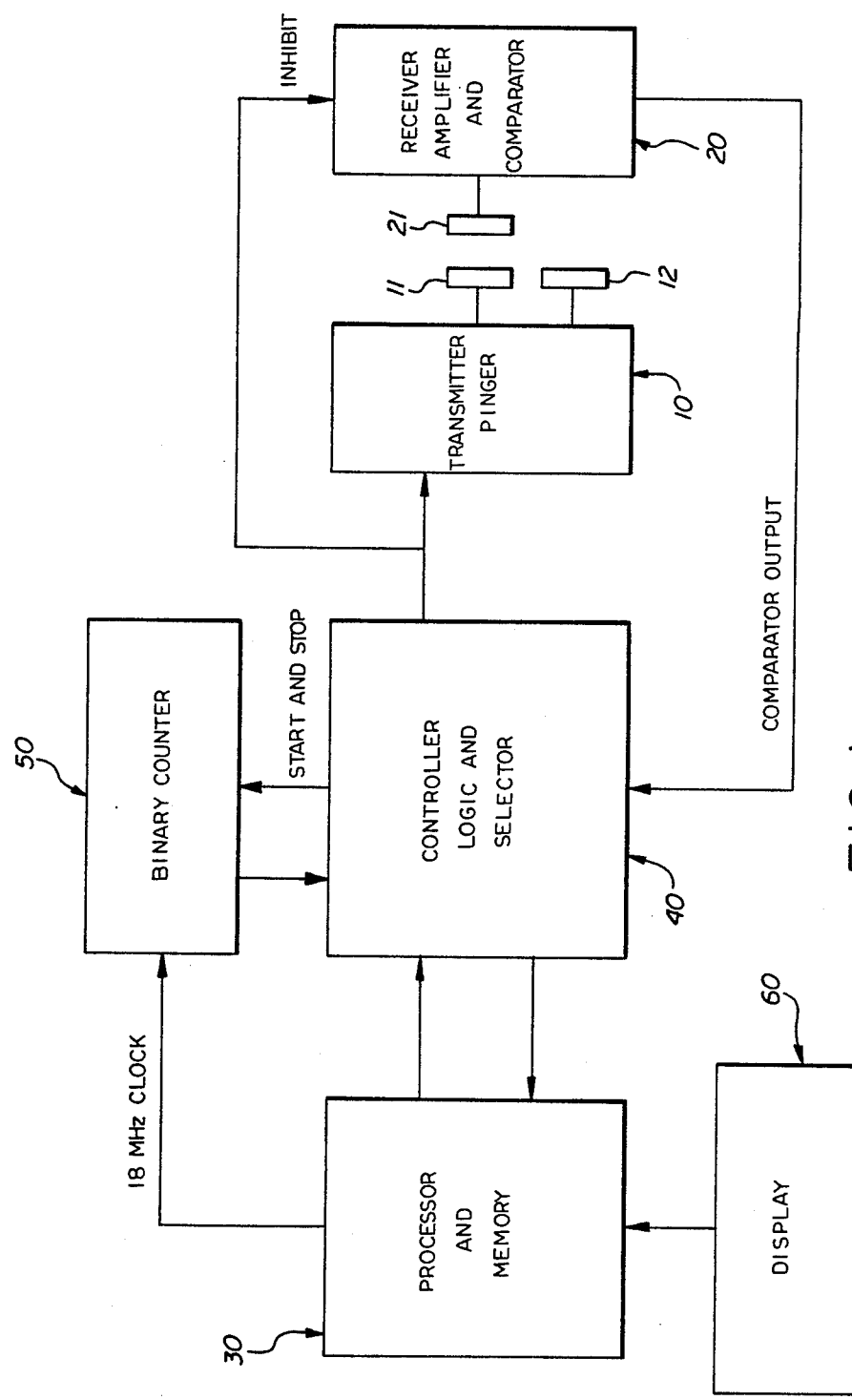
FIG. 1 is a block diagram of the ultrasonic apparatus, computer and related electronic circuitry of the present invention, according to a preferred embodiment thereof.

Referring first to the block diagram of FIG. 1, the measuring apparatus of the present invention comprises transmitting means 10 for generating and transmitting ultrasonic or acoustic pulses and a receiver means 20 for receiving such acoustic pulses. The transmitter means 10 includes first and second transducers 11 and 12 and the receiver means includes a receiver crystal 21. The location and function of the transducers 11 and 12 and crystal receiver 21 will be more fully explained hereafter.

The system of the present invention also includes computer means for computing the cross-sectional area of a measured limb by utilizing signals derived from the receiver means 20. Connected to the transmitter means 10, receiver means 20 and computer means 30 is a controller means 40, the purpose of which is to control the flow of information through the measuring system, to selectively activate one of the transducers 11 or 12 and to provide a count proportional to measured ultrasonic transit time for display. Its composition and function will be more fully described hereafter. A binary counter 50 is connected to the controller means 40 and computer means 30.

Connected to the computer means 30 is display means 60 for visual display of the area computed by the computer means 30. The display 60 and the other electronic components shown in FIG. 1 will be more fully described hereafter.

Figure 2:
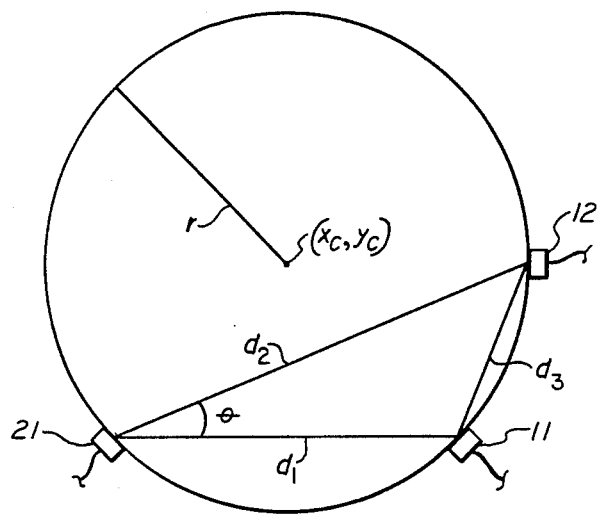
FIG. 2 is a circular representation of a cross-sectional limb area for explaining the computational scheme of the present invention.

To better understand the operation of the measuring system of the present invention, reference is now made to FIG. 2 in which a circle C is shown representing the cross-sectional area of a limb, e.g. the calf region of a lower limb. The radius of the circle C is r, and the center of the circle is located at coordinates $(x_c, y_c)$. The measuring system of the present invention will calculate the area of the circle C, thus closely approximating the cross-sectional area of the limb represented thereby and giving an accurate indication of the volume changes of such limb. The calculation is made utilizing two independent chord length measurements of the circle C.

To make the necessary chord measurements, the transducers 11 and 12 are positioned on the surface of the limb or circle C at a predetermined distance therebetween. The receiver crystal 21 of the receiver means 20 is also placed on the surface of the limb. The distance between transducer 11 and receiver crystal 21 is represented by the chord $d_1$ and the distance between the transducer 12 and receiver crystal 21 is represented by the chord $d_2$. The angle between chords $d_1$ and $d_2$ is $\theta$. The distance between transducers 11 and 12, represented by a third chord $d_3$, is predetermined and accurately known.

If pulses are generated at the transducers 11 and 12 and the travel time of such acoustic pulses along the first and second chords $d_1$ and $d_2$ to the receiver crystals 21 is accurately measured, the length of chords $d_1$ and $d_2$ can be determined from the formulas:

$$d_1 = t_1 v$$

and $$d_2 = t_2 v$$

where:
$t_1$ and $t_2$ are times required for the ultrasonic pulses to be received from the transducers 11 and 12, respectively; and
v is the velocity of sound in tissue.

The velocity of sound in the gastrocnemius muscle at 2.25 MHz and 23° C. is 1564 m/sec. The temperature dependence of average sound velocity in the range of 20° to 40° C. shows a variation of less than 2 m/sec/°C. For a medium temperature difference of ±2° C., the error involved in the distance measurements of 10 cms and above is less than 0.25%. However, even this change in body temperature during measurements is not anticipated. It will be noted that the measurement medium is living tissue. Hence, temperature related errors are of no significant concern in limb cross-section computations.

Without any loss of generality, it can be assumed that the chord $d_1$ defines the axis. Thus, the x coordinate $(x_c)$ of the center of the circle equals $d_1/2$. The equation of the circle passing through the intersections of chords $d_1$, $d_2$ and $d_3$ with its center at $(x_c, y_c)$ can be expressed as:

$$(x - x_c)^2 + (y - y_c)^2 = r^2 \quad (1)$$

where r is the radius of the circle.
For the given points:

$$(d_1/2)^2 + y_c^2 = r^2 \quad (2)$$

$$(x_2 - d_1/2)^2 + (y_2 - y_c)^2 = r^2 \quad (3)$$

Also $$d_3^2 = d_1^2 + d_2^2 - 2d_1 d_2 \cos\theta \quad (4)$$

Finally, from equations (2) and (3), we can write:

$$(x_2 - d_1/2)^2 + (y_2 - y_c)^2 = (d_1/2)^2 + y_c^2 \quad (5)$$

Solving for $y_c$ we have:

$$y_c = \frac{d_2^2 - x_2 d_1}{2y_2} = \frac{d_2^2 - d_2 \cos\theta d_1}{2d_2 \sin\theta} \quad (6)$$

The area of the circle is given by $$\pi r^2 \text{ or } \pi(x_c^2 + y_c^2) \quad (7)$$

The chord lengths $d_1$ and $d_2$ are measured quantities. The chord length $d_3$ is a deisgn distance (known) between transducers 11 and 12. Therefore, the coordinates $(x_c, y_c)$ of the center and the cross-sectional area of the circle C can be computed.

Equations (6) and (7) are simulated on the computer means 30 for computational accuracy using various chord length sizes. All calculations are carried out in floating point arithmetic with an accuracy of 1 part in $10^5$. The program written in assembly language using an Intel 8080 microprocessor chip takes approximately 1500 words of memory space. The accuracy of computation compared with those using a DEC PDP-11 computer are in excellent agreement. The error in area computations using $d_1 = 6.45$ cm; $d_2 = 7.55$ cm; and $d_3 = 1.85$ cm is $5 \times 10^{-4}$% (an insignificant amount). It has been observed that these computations are affected by accuracy in the measurement of the distance $d_3$. Such measurement must be accurate to within 0.1 mm. A large $d_3$ provides very accurate computations but leads to practical problems in the design of ultrasonic transducers and crystals. A $d_3$ in the order of 2.5 cm has turned out to be a good compromise.

Referring now again to FIG. 1, the electronic components of the system of the present invention will be described in greater detail. The computer means 30 may comprise one 8-bit 8080 microprocessor chip; two 8-bit 2708 EPROM (Erasable Program Read Only Memory) chips (these store preprogrammed instructions and constants), two 4-bit 2111 RAM (Random Access Memory) chips for storage of generated data, one 8228 data bus and status controller and an 8224 clock generator (provides the working clock at 2 MHz for the CPU 8080 microprocessor chip and supplies the clock frequency for the counter 50 at 18 MHz). The computer means 30 may also contain a 6820 Motorola PIA (Peripheral Interface Adapter) which drives four BCD to seven segment decoders (7448 NS National Semiconductor). The interface between EPROMs, RAMs, PIA, and CPU is logically controlled by two 7400 NS and one 7402 Signetic SSI logic gates. The power for all units may be derived from a TM 515 power module with suitable regulators to obtain ±12 V and ±5 V.

The heart of the computer means 30 is the 8080 CPU chip. An 8080 chip is a complete 8-bit parallel CPU for use in general purpose computing and is operated by 8 to 24 bit long externally applied instructions. The two EPROMs are used to store the desired instructions to operate the CPU, together with the needed constants (e.g. $\pi$, velocity of sound, etc.). The data lines between the CPU and EPROMs are latched through the 8228 data bus controller which translates the status from the CPU to either external memory units of the peripheral devices (e.g. input/output) for a preprogrammed sequence of operaton. The 8228 data bus also acts as a data buffer and provides a greater drive capacity for an 8-bit data bus from the CPU (which has approximately 1.9 ma capacity, not enough to drive more than a single TTL gate).

The sequence of system operation is governed by an internal 16-bit program counter register (within the CPU) which can be reset externally. The 16-bit contents of the program counter are sensed by the EPROMs or the RAMs through a logic decoding network. In the present system, an SPST (Single Pole Single Throw) pushbutton switch is provided for resetting the instrument. All the intermediate variable data needed for both the operation of the CPU and the ultrasonic transit time computation are stored in the two RAMs.

As previously stated, the function of the controller means 40 is to control the flow of information throughout the system, to select a particular transducer 11 or 12 for chord length measurement and to provide a count proportional to measured ultrasonic transit time for display. The controller means 40 may contain three 4-bit 7493 binary counters connected in series (cascade). The basic counter frequency is 18 MHz, hence the accuracy of time measurements is $\pm 5.5$ m/sec. The binary counters are interfaced with the CPU of the computing means 30 through a 6820 PIA (Peripheral Interface Adaptor). A 7474 flip flop, which is set by a transmitter enabled pulse from the CPU, is used to start the counters. The flip flop is reset by a pulse from the receiver-comparator electronics which stops the counter. (The status of binary counters is relayed to the computer means 30 by means of a flag signal from 7474 flip flop in order for efficient transfer of data for computation of area.)

The receiver means 20 includes a receiving amplifier and a comparator circuit. Because the receiving amplifier has high gains, the possibility of false output from the comparator due to the presence of low level unwanted interference may exist during the activation phase of the transmitted signal. To avoid this possibility the controller means 40 may include a 74121 One Shot which inhibits the receiver means 20 during this period (its duration is adjustable). A CD 4052 analog switch is used for selected activation of either the first or second transducers 11 and 12, respectively. (Actually, the CD 4052 analog switch can provide up to four separate transmitter/transducers.) A 7400 gate provides the required interface logic between the binary counters, flip flop, One Shot and analog switch. Two transistors (2N2222) may be used to convert the logic levels from the analog switch to a 15 V pulse to activate the ultrasonic Pinger or transmitting means 20.

Figure 3:
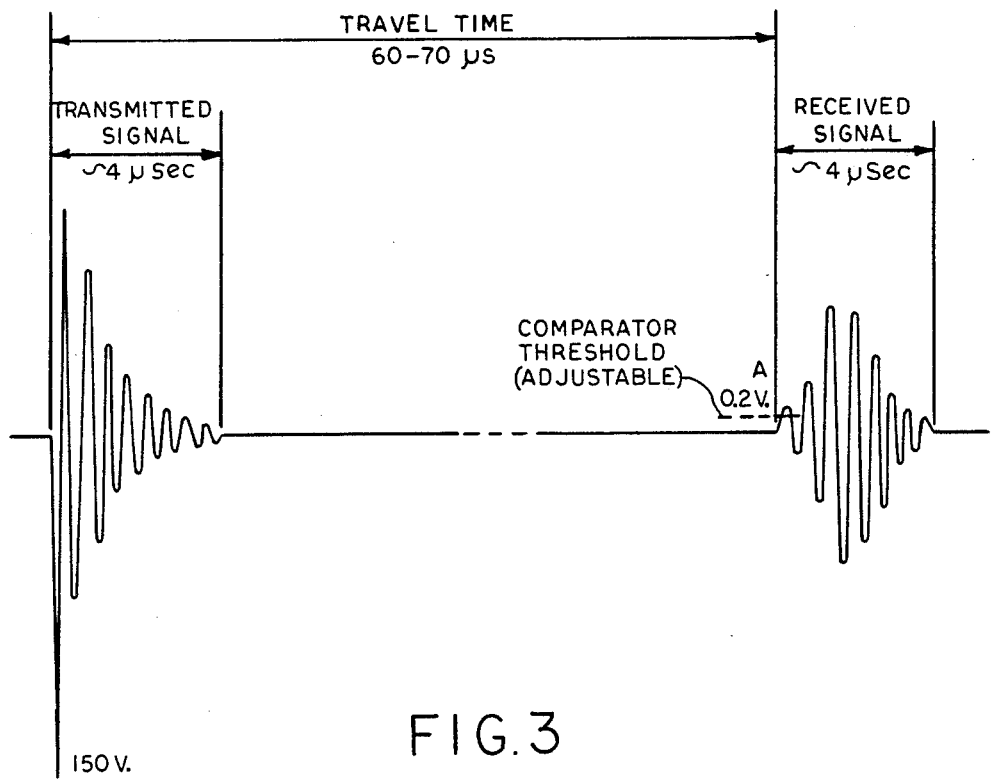
FIG. 3 is a time diagram, illustrating typical ultrasonic signals transmitted and received in the present invention.

As previously mentioned, the ultrasound received by the receiver means 20 is amplified and used in a comparator to produce an outgoing pulse to stop the counter 50. A typically received signal is shown in FIG. 3. Point A shows the arrival of an ultrasonic pulse at the receiver means 20. The threshhold of the comparator is usually set at about 0.2 volts in order to avoid false triggering. Measurements have shown that the first peak has an amplitude of about 0.5 volts. Thus, the maximum error due to threshhold adjustment is limited to the $\lambda/4$ where $\lambda$ is the wavelength of ultrasound. The ultrasonic frequency used in the ULVS range from 2–3 MHz implies a maximum error of 0.2 mm. It should be noted that this error can be minimized by the operator through the adjustment of threshhold and optimization of transducer location.

Upon computation of the desired cross-sectional area, the results are transferred to the PIA (Peripheral Interface Adapter) of the computer means 30 and to the display means 60. The display means 60 may be a numeric display which can be built into the system using a commercially available LED display.

Thus, the measurement of limb volume changes can be accurately computed by the system of the present invention by on-line computation of the cross-sectional area of a limb. The measurement is nonintrusive, safe and reliable. The measurement technique is applicable to both earth and space environments. It is easy to operate and calibrate.

Although the system of the present invention was originally developed for space applications, a broad range of applications in the medical field is clearly evident. Since the system does not confine limb movement, new tests in exercise physiology can relate changes in limb volume to activity level. Since the system can precisely detect very small changes in limb cross-section, many as yet undiscovered cause-effect relations in muscle physiology can now be researched. Coronary insufficiency oftentimes causes fluids to collect in the extremities (called pitting edema). Various drugs are used to disperse the fluid and the reported device can be used to measure the efficacy of these drugs by monitoring decrease in limb volume. A myopathy such as muscular dystrophy and neurological disorders such as multiple sclerosis and stroke can cause muscle wasting and atrophy. The system of the present invention can monitor both the degradation and the improvement through rehabilitation.

While a single embodiment of the invention has been described herein, there are many variations thereof which can be made, particularly in the electronic circuitry thereof, without departing from the spirit of the invention. Therefore, it is intended that the scope of the invention be limited only by the claims which follow.

We claim:

1. Measuring apparatus for determining changes in the volume of limbs or other body extremities by determining the cross-sectional area of such limbs comprising:

transmitting means including first and second transducers for positioning on the surface of said limb at a predetermined distance therebetween;

receiver means including a receiver crystal for positioning on the surface of said limb, the distance between said receiver crystal and said first and second transducers being represented by respective first and second chords of a cross-section of said limb, said predetermined distance between said first and second transducers being represented by a third chord of said limb cross-section;

means for generating acoustic pulses from said first and second transducers along said first and second chords to derive from said receiver means first and second signals related to the travel time of said acoustic pulses along said first and second chords respectively; and computer means connected to said receiver means for computing the area of said limb cross-section utilizing said first and second signals.

2. Measuring apparatus as set forth in claim 1 in which said computer means includes circuit means for determining the area of a circle by solving the equation $$A = \pi(x_c^2 + y_c^2)$$

where:

A is area; and $x_c$ and $y_c$ are the x and y coordinates, respectively, of the center of a circle having three chords coinciding with said first, second and third chords of said limb cross-section.

3. Measuring apparatus as set forth in claim 1 in which said computer means includes a memory circuit for storing constants for modifying said first and second signals by a constant factor.

4. Measuring apparatus as set forth in claim 3 in which said constant factors include $\pi$ and the velocity of sound in the flesh medium of said limb or body extremity.

5. Measuring apparatus as set forth in claim 1 including controller means connected to said transmitter, receiver and computer means including circuitry for sequentially activating said first and second transducers for generation of said acoustic pulses along said first and second chords.

6. Measuring apparatus as set forth in claim 5 in which said controller means includes counter means activated by said acoustic pulses and by which said travel time of said acoustic pulses along said first and second chords is determined.

7. Measuring apparatus as set forth in claim 6 in which said receiver means includes a comparator circuit by which said counter means is deactivated upon arrival of said acoustic pulses at said receiver crystal.

8. Measuring apparatus as set forth in claim 7 in which said controller means includes an inhibitor circuit connected to said receiver means for inhibiting said comparator when receiving low level interference signals.

9. Measuring apparatus as set forth in claim 1 including display means connected to said computer means for visually indicating said cross-sectional limb area.

10. Measuring apparatus as set forth in claim 9 in which said display means includes a LED numeric display on which said cross-section limb area is visually displayed.

* * * * *